United States Patent [19]

Errico et al.

[11] Patent Number: 5,707,372

[45] Date of Patent: Jan. 13, 1998

[54] MULTIPLE NODE VARIABLE LENGTH CROSS-LINK DEVICE

[75] Inventors: Joseph P. Errico, Far Hills; Thomas J. Errico, Summit; James D. Ralph, Oakland; Steve Tatar, Montville, all of N.J.

[73] Assignee: Third Millennium Engineering, LLC., Summit, N.J.

[21] Appl. No.: 772,408

[22] Filed: Dec. 23, 1996

Related U.S. Application Data

[63] Continuation-in-part of Ser. No. 677,812, Jun. 20, 1996.

[51] Int. Cl.[6] ............................................ A61B 17/70
[52] U.S. Cl. ...................... 606/61; 606/60; 606/72; 606/73; 606/69
[58] Field of Search .................... 606/60, 61, 69, 606/70, 71, 72, 73

[56] References Cited

U.S. PATENT DOCUMENTS

| | | | |
|---|---|---|---|
| 5,261,907 | 11/1993 | Vignaud et al. | 606/61 |
| 5,306,275 | 4/1994 | Bryan | 606/61 |
| 5,312,405 | 5/1994 | Korotko et al. | 606/61 |
| 5,368,594 | 11/1994 | Martin et al. | 606/61 |
| 5,498,263 | 3/1996 | DiNello et al. | 606/69 |
| 5,531,745 | 7/1996 | Ray | 606/61 |
| 5,607,425 | 3/1997 | Rogozinski | 606/60 |

*Primary Examiner*—Michael Buiz
*Assistant Examiner*—Daphja Shai
*Attorney, Agent, or Firm*—Joseph P. Errico, Esq.

[57] ABSTRACT

A compression locking variable length cross-link device having modular components, including rod and/or pedicle screw coupling elements each having a hole which may be disposed co-linearly with respect to other such holes in opposing elements such that a threaded hinge-post may be inserted therein. A nut is utilized to compress the elements together to rigidly secure the elements once they have been properly positioned relative to one another. In an additional set of embodiments, a linkage member having an elongate hole therein may be used to couple similar elements thereto in a similar flexible hinge-post manner such that the elements may be coupled to the linkage member instead of to the opposing elements directly.

15 Claims, 4 Drawing Sheets

MULTIPLE NODE VARIABLE LENGTH CROSS-LINK DEVICE

CROSS-REFERENCE TO RELATED APPLICATION

This application is a continuation in part of co-pending application U.S. Ser. No. 08/677,812 still pending filed Jun. 20, 1996 entitled "A Hinged Variable Length Cross-Link Device".

BACKGROUND OF THE INVENTION

1. Field of the Invention

This invention relates generally to a mechanical cross-link device for use with dual rod orthopaedic implant apparatus. More particularly, this invention relates to a novel device which is fixed to each rod of a dual rod implant apparatus, or to the pedicle screws through which each one of a dual rod apparatus are positioned, respectively, to enhance the rigidity of the apparatus.

2. Discussion of the Prior Art

The bones and connective tissue of an adult human spinal column consist of an upper portion (the cervical, thoracic, and lumbar regions) having more than 20 discrete bones, and a lower portion which consists of the sacral bone and the coccygeal bodies. The bones of the upper portion are generally similar in shape, the size of the bones progressively varying from small to large downwardly along the spine.

The vertebrae are coupled to one another by a tri-joint complex consisting of an anterior disc and the two posterior facet joints, the anterior discs of adjacent bones being cushioned by cartilage spacers referred to as intervertebral discs. In its entirety, the spinal column is highly complex in that it houses and protects critical elements of the nervous system which have innumerable peripheral nerves and arterial and venous bodies in close proximity. In spite of these complexities, the spine is a highly flexible structure, capable of a high degree of curvature and twist through a wide range of motion. Genetic or developmental irregularities, trauma, chronic stress, tumors, and disease, however, can result in spinal pathologies which either limit this range of motion, or which threaten the critical elements of the nervous system housed within the spinal column. A variety of systems have been disclosed in the art which achieve this immobilization by implanting artificial assemblies in or on the spinal column.

A variety of systems have been disclosed in the art which achieve this immobilization by implanting artificial assemblies in, or on, the spinal column. These assemblies may be classified by their position relative to the spine, as anterior, posterior, or lateral implants. Anterior and lateral assemblies generally comprise short structures which support only a few adjacent vertebral bodies. Conversely, posterior implants often comprise pairs of elongate vertically aligned rods for stabilizing both short and long segments of the spine. Such posterior rods are coupled to the back of the spinal column via hooks which slip under the lamina, means for attaching to the transverse process, and/or by screws which are inserted through the pedicle bone. In order to provide enhanced torsional rigidity, these apparatus generally include cross-linking devices which couple the rods together transverse to the axis (vertical axis) of the apparatus.

Referring now to FIG. 1, U.S. Pat. No. 5,005,562 to Cotrel teaches such a dual rod apparatus which includes cross-link devices 38a,38b. These cross-link devices 38a,38b each include a pair of U-shaped gripping element 35a,35b which may receive the rod 30a,30b respectively. Each of the gripping elements includes a first threaded hole which extends from the outer lateral surface into the inner surface of the U-shaped rod receiving region. The gripping elements 35a,35b are fixed to the rods 30a,30b by set screws 37a,37b which are positioned in the first holes such that tightening of the set screws locks the rod 30a,30b in the gripping element. The gripping elements 35a,35b are coupled together by a threaded rod 33 which permits the gripping elements to be selectively spread or brought closer together, in accordance with the relative position of the rods 30a,30b. The threaded rod 33 extends through a second set of threaded holes in the gripping elements 35a,35b.

The bulkiness of each of the gripping elements 35a,35b, required so that it may receive the threaded rod 33, is difficult for the surgeon to use easily under operative conditions. This difficulty is dramatically enhanced by the closeness of the rods in the cervical spine. The size of the gripping elements, and the relative position of the set screws often cause substantial difficulty with respect to the tightening of same because of their positions relative to the operative access. This bulkiness also reduces available bone graft surface area, which is critical for a successful fusion and long term immobilization. In addition, in order for a surgeon to selectively vary the spread or position the gripping elements 35a,35b, one of the gripping elements must be translated relative to the other, thus requiring the cross-link to be removed (loosening the set screws and withdrawing the device entirely from the operative site). This is particularly burdensome with respect to providing the surgeon with the ability to apply an inward force to the rods 30a,30b as the spread may not be varied in situ. In addition, the ability to angulate the device around the spinous process or to conform to non-parallel rods is desirable.

It is also an unfortunate feature of many such devices of the prior art that they are only able to couple to each rod at one point. It is, therefore, a principal object of some of the embodiments of the present invention to connect to each rod at at least one point.

It is also, therefore, a principal object of the present invention to provide a new and novel cross-link device which provides a less bulky profile, therein permitting its inclusion many areas of the spine wherein prior cross-link devices are not positionable.

It is further an object of the present invention to provide a cross-linking device which admits increased area for bone grafting.

It is also an object of the present invention to provide a cross-link device which provides the surgeon with the ability to lock the device to the rods more easily than prior cross-link devices.

It is also, therefore, an object of the present invention to provide a cross-link device which provides the surgeon with the ability to vary the spread or angulation of the rod gripping or pedicle screw coupling portions in situ, so that in doing so, the surgeon is not required to withdraw the device from the patient.

Other objects of the present invention not explicitly stated will be set forth, and will be more clearly understood, in conjunction with the descriptions of the preferred embodiments disclosed hereafter.

SUMMARY OF THE INVENTION

The preceding objects of the invention are achieved by the present invention which is a variable length cross-link device which may be affixed to the rods of a dual rod implant apparatus, or to the heads of opposing pedicle screws through which such rods are positioned. The present invention may be practiced in a variety of different embodiments, some of which permit multiple point connection to each rod; the several enclosed herein being representative of preferred ones of the invention.

The device is capable of assuming a variable length and a variable angulation. More specifically, the device comprises at least two equivalent rod hooking or pedicle screw coupling elements which are coupled together with at least one sliding and locking hinge post. The first ends of these elements comprise either a hooking conformation to receive therein and/or seat against and hook to the circumferential surfaces of the rods of a dual rod apparatus, or a loop which seats around the head of the corresponding pedicle screw about which it is positioned. Set screws may be incorporated in embodiments in which the first ends of the elements hook to the rod to lock thereto.

At the opposite end of the first element from the rod or pedicle screw coupling site, there is a flat extending member having a hole therethrough. In some embodiments this hole is elongate, and in others it is round. An optional flat member having an elongate hole or slot therein is also provided for use in certain embodiments. In all embodiments, the coupling is a hinge-type wherein the holes in the second ends of the elements are positioned co-linearly (along with the hole in the optional flat member when used) such that a shaft may be positioned through the combined axial passageway. The shaft is slideable within the elongate through in the holes while the elements are angulateable and translatable relative to one another.

The shaft which is disposed in the axial passage formed by the co-linear holes of the elements includes a thickened bottom end portion having a diameter greater than the width of the holes in the elements. This thickened portion prevents the shaft from being removable through the top of the mutual passageway formed by the coupled elements. The top of the shaft, which extends above the co-linear holes includes a threading. When engaged by a nut thereon the hinge-post shaft is prevented from being removed from the co-linear holes at both ends. The contact pressure of the nut onto the extending portion of the upper element and the oppositely directed pressure from the thickened portion at the bottom of the shaft against the lower extending portion, provides a compression force between the sandwiched elements. Prior to complete nut tightening, the elements are slideably coupled together. Continued tightening of the nut causes the coupled elements to be completely locked to one another.

It shall be understood that a variety of alternate embodiments are possible given the combination of modular elements set forth above, however, the combinations set forth in the following Detailed Description are preferred embodiments of the present invention.

DETAILED DESCRIPTION OF THE PREFERRED EMBODIMENT

While the present invention will be described more fully hereinafter with reference to the accompanying drawings, in which particular embodiments and methods of implantation are shown, it is to be understood at the outset that persons skilled in the art may modify the invention herein described while achieving the functions and results of this invention. Accordingly, the descriptions which follow are to be understood as illustrative and exemplary of specific structures, aspects and features within the broad scope of the present invention and not as limiting of such broad scope.

Figure 1:
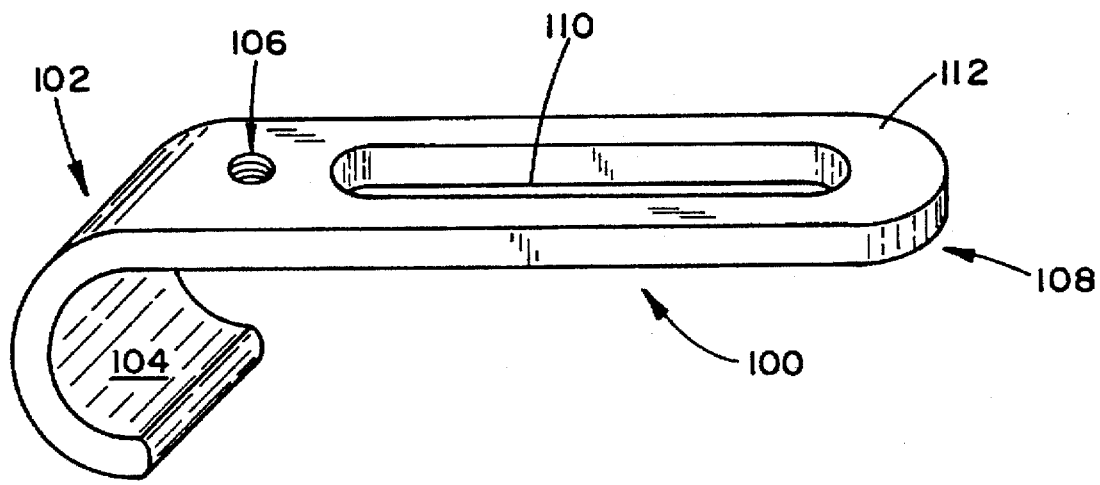
FIG. 1 is a side perspective view of a first rod hooking element which is an aspect of the present invention.

As previously stated, the present invention has various embodiments each comprising a plurality of modularized elements which, when assembled, each embodiment utilizes a similar locking mechanism. The modular elements shall be set forth and described individually and in conjunction with functional embodiments hereinbelow. Referring now to FIG. 1, a first element 100 of one of the embodiments of the present invention is provided in a side perspective view. As with all elements of this invention, the material of which this element 100 may comprise a high strength material, for example medical grade steel or titanium compounds, which has been found ideally suited for implantation into the human body. The first end 102 of the element 100 has a C-shaped for seating against a rod. More specifically, the C-shaped end 102 comprises a hook-shaped conformation having an inner surface 104 which is contoured to seat against the surface of a rod. A threaded through hole 106 is provided at the junction of the hook-shaped end and the remainder of the element; the through hole 106 being ideally suited to receive a threaded set screw (see FIG. 2) to secure a rod in the hook-shaped portion once it has been positioned therein.

The other end of the element 100 comprises an elongate flat segment 108 having an elongate hole or slot 110 formed therein, coaxial with the long axis of the segment 108 and the hole 110 extending through the segment from the top surface 112 to the bottom (not shown).

Figure 2:
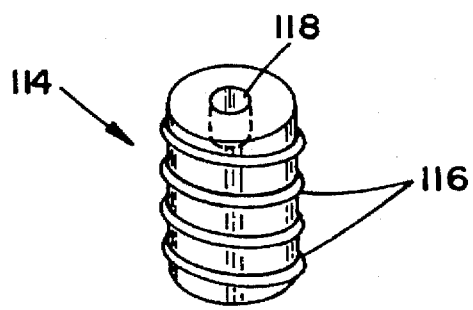
FIG. 2 is a side view of a set screw which is another aspect of the present invention.

Referring now to FIG. 2, the set screw 114, which is utilized to lock the rod in the hook-shaped end 102 of the element 100 via compression is shown in a side view. The set screw 114 comprises a cylindrical slug having a surface threading 116 which is ideally suited to the threading of the through hole 106. The screw 114 further includes a recess 118 in the top thereof, the recess having an internal conformation which may be engaged by a suitable tool for applying a torsional force thereto, for example a slot for a screwdriver or a hexagonally angled interior wall for an allen wrench.

Figure 3:
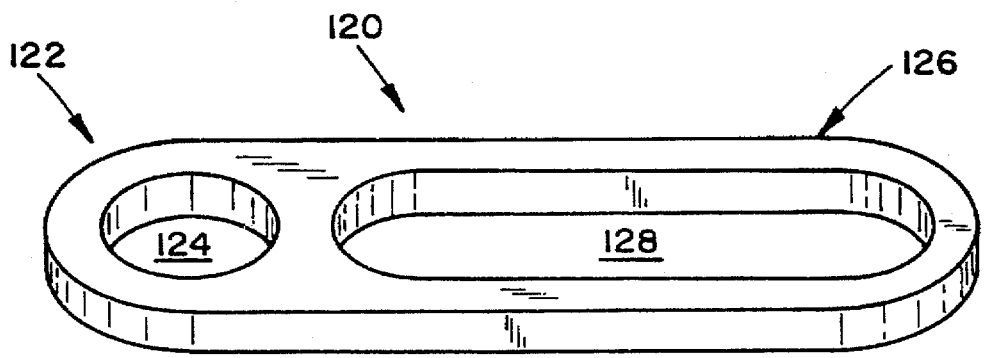
FIG. 3 is a side perspective view of a first pedicle screw mounting element which is an aspect of the present invention.

Referring now to FIG. 3, an alternative element 120, is shown in a side perspective view. More specifically, the second element 120 comprises a first end 122 which is flat and includes a circular hole 124 therein. The hole 124 is sized to fit around the unsecured head of a pedicle screw, so that it may be coupled to one of the dual rods of a dual rod apparatus via the locking of the pedicle screw rod coupling means (often a locking nut). The second end of this alternative element 120 is substantially similar to the second end of the element 100 illustrated in FIG. 1. More particularly, the second end comprises a flat segment 126 having an elongate hole or slot 128 extending coaxially with the long axis of the element 120.

In its assembled state, a first set of embodiments, to be more fully described hereinafter the description of other critical components, includes at least two of these elements 100 or 120 positioned with the bottom surface of one element 100,120 is seated against the top surface of another element 100,120 such that the elongate holes 110 and/or 128 are aligned so as to form a passageway through which a hinge post (see FIGS. 4 and 6 which are described more fully hereinbelow) may be axially positioned therethrough.

Figure 4:
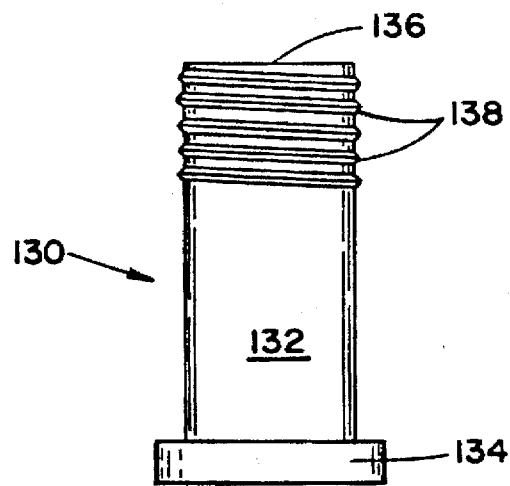
FIG. 4 is a side view of a post which is used in conjunction with an embodiment of the present invention.
Figure 5:
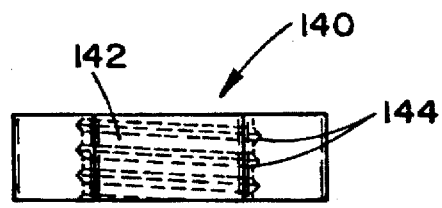
FIG. 5 is a side view of a top locking nut which threadably mates to an upper portion of the post of FIG. 4.

Referring now to FIGS. 4 and 5, the hinge post (or shaft) 130 and the locking nut 140 are shown in side views. Specifically with respect to FIG. 4, a hinge post 130 is provided to be inserted through the aligned through holes 110 and/or 128 of the at least two elements 100 and/or 120. The hinge post 130 has a cylindrical body 132 of generally constant diameter which is desirably substantially equivalent to or slightly smaller than the narrowest width of the elongate holes 110,128. The bottom end 134 of the post 130, however, is thickened (wider) such that its diameter is larger than the hole 110,128 in the second ends 108,126 of the elements 100,120, respectively. The upper end 136 of the post 130 includes a threading 138.

The nut of FIG. 5 comprises a cylindrical member having an axial bore 142 having a threading 144 disposed on the inner surface thereof. This threading 144 is suited for rotationally engaging the threading 138 of the post 130 such that the nut 140 may be threadably translated along the axis of the post 130.

Figure 6:
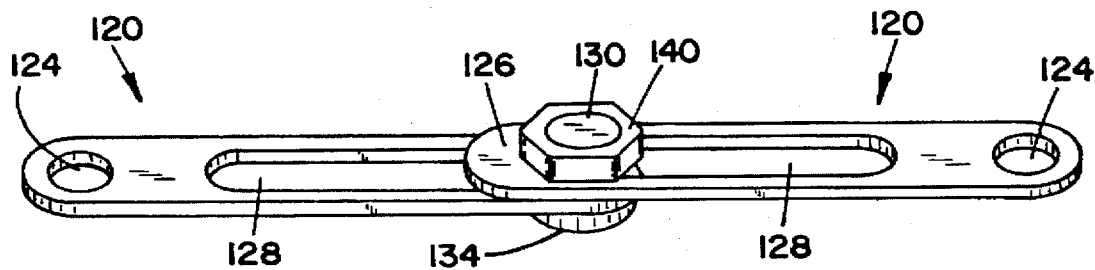
FIG. 6 is a side perspective view of a fully assembled embodiment of the present invention comprising the elements illustrated in FIGS. 3–5.

Referring now to FIG. 6, a first embodiment of the present invention is shown in a side perspective view. In this embodiment two elements 120 of the type which can be coupled to the head of a pedicle screw are utilized. The elements 120 are positioned with elongate segments 126 facing one another such that the elongate holes 128 form a passageway through which the post 130 is inserted. The threaded upper portion 136 extends above the top surface of the uppermost element 120 and the widened bottom end 134 of the post 130 comes into contact with the bottom surface of the element 120. The nut 140 is first advanced into initial contact with the top surface of the uppermost element 120 such that the post 130 is prevented from being removed from the passageway mutually defined by the elongate holes 128 of the elements 120, but remains slideable therein such that the elements 120 may be translated and/or angulated relative to one another in order that the holes 124 in the first ends may be selectively and desirably positioned over, and secured to, the heads of corresponding pedicle screws. The locking nut 140 is then tightened onto the post 130 thereby providing a mutually compressing pressure between the bottom 134 of the post and the nut 140. This compression force is applied against each of the elements 120 such that they are compression locked together.

Figure 7:
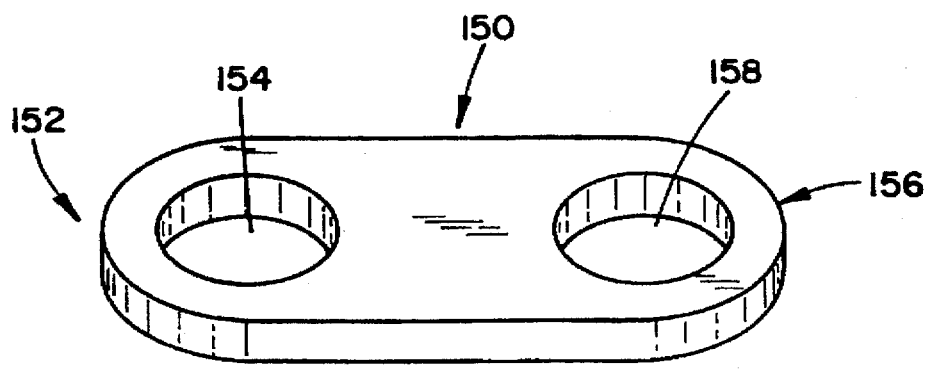
FIG. 7 is a side perspective view of an alternative element which is an aspect of the present invention.

Referring now to FIG. 7, another pedicle screw securing element 150 of the present invention is provided in a side perspective view. This element 150 comprises a flat conformation having a first end 152 with a hole 154 which is suited for coupling to the head of a pedicle screw (much like the previously described elements 120 illustrated in FIGS. 3 and 6). The second end 156, however, includes a through hole 158 which is round, i.e. not elongate. This hole 158 has a diameter which is substantially equal to, or slightly larger than, the diameter of the post 130, but less than that of the base portion 134 thereof.

Figure 8:
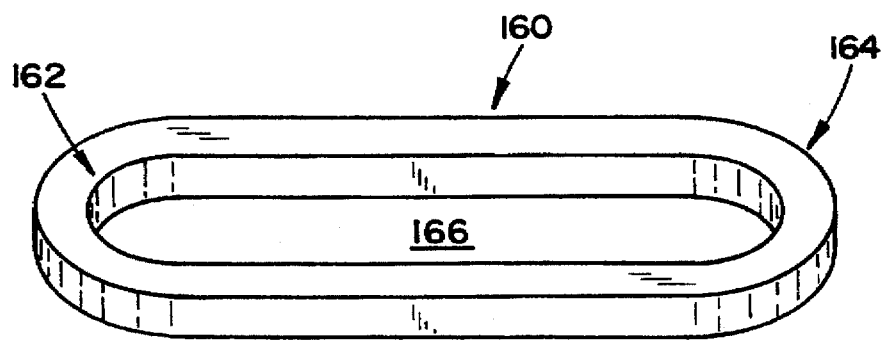
FIG. 8 is a side perspective view of an optional flat member of the present invention.

Referring now to FIG. 8, a linkage member 160 is provided in a side perspective view. This linkage member 160 is flat and elongate having first and second ends 162 and 164, respectively. An elongate hole 166, similar to the elongate holes 110 and 128 of the previously described elements 100 and 120, respectively, is provided as well.

Figure 9:
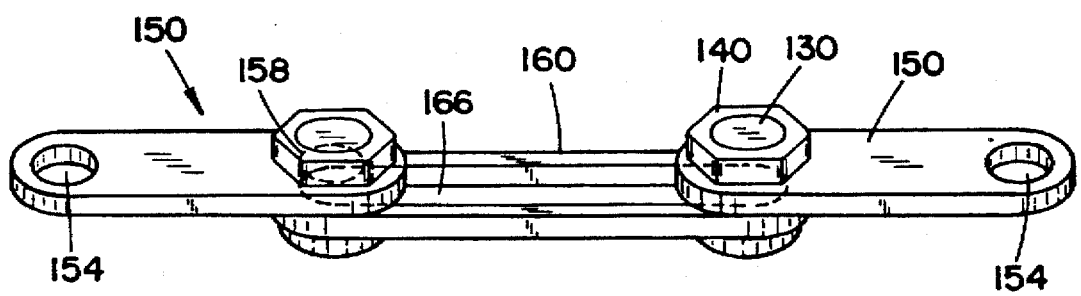
FIG. 9 is a side perspective view of another fully assembled embodiment of the present invention which includes the elements illustrated in FIGS. 4, 5, 7, and 8.

Referring now to FIG. 9, a side perspective view of another embodiment of the present invention is provided. In this embodiment a pair of pedicle screw coupling elements 150 having round through holes 158 are disposed at opposing ends 162 and 164 of the linkage member 160. These elements 150 are positioned such that the round holes 158 of each are disposed above (or, in the alternative, below) the elongate hole 166 of the linkage member 160 such that two distinct passageways are provided. Two post members 130 are provided, one passing through each of the passageways formed by the holes 158 and the corresponding portions of the elongate hole 166. Nuts 140 are initially advanced onto the threaded top portions 136 of the posts 130 so that the opposing upper and lower surfaces of the linkage member and the elements 150 are held together. It shall be understood that prior to tightening the elements 150 are free to slide along the surface of the linkage member 160 as the post 130 slides within the elongate hole 166. This permits independent rotation and translation of the two members 150 relative to one another. As previously described, tightening of each of the nuts 140 causes the corresponding element 150 to be locked via compression to the linkage member 160.

Figure 10:
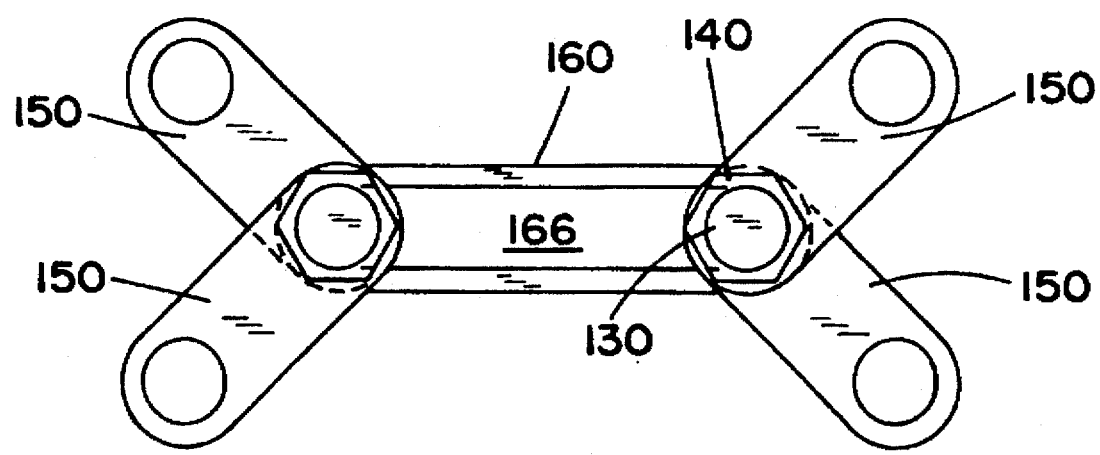
FIG. 10 is a top view of another fully assembled embodiment of the present invention which includes the elements illustrated in FIGS. 4, 5, 7, and 8.

Referring now to FIG. 10, a top view of an alternative variation of the present invention is illustrated in which multiple elements 150 are provided at each end 162,164 of the linkage member 160. More specifically, this embodiment includes a pair of elements 150 at each end 162,164, positioned such that a single post 130 couples both of the elements 150 to the linkage member 160. This assembly permits multiple pedicle screws on each side of a dual apparatus to be linked to one another, and to other pedicle screws on the other side of the dual rod apparatus. This provides additional security against any individual component failure, while still providing maximal flexibility with respect to secure fixation.

While there have been described and illustrated cross-link devices for coupling dual rods of orthopaedic apparatus together and providing enhanced stability thereto, it will be apparent to those skilled in the art that variations and modifications are possible without deviating from the broad spirit and principle of the present invention which shall be limited solely by the scope of the claims appended hereto.

We claim:

1. A variable length cross-link device for use with orthopaedic rod apparatuses having a pair of rods, comprising:

at least two coupling elements each having first and second ends, said first ends of each having means for securing to alternative ones of said pair of rods, and said second ends having elongate through holes, at least two of said elongate holes being disposed co-linearly so as to mutually define a passageway;

at least one hinge-post member positionable in said passageway, such that said corresponding at least two coupling elements may translate as said hinge-post slides within said elongate holes and such that said corresponding at least two coupling elements may angulate relative to one another around said hinge-post; and at least one locking means, mateable with said hinge-post such that when said locking means is engaged thereonto, the corresponding at least two coupling elements are compressed together and thereby crush-locked together and prevented from further relative motion.

2. The device as set forth in claim 1, wherein said first ends of said at least two coupling elements comprises a hook-shaped conformation and wherein said means for securing same to alternate ones of said rods comprises a set screw.

3. The device as set forth in claim 1, wherein said first ends of said at least two coupling elements each comprises a circular hole which permits each of said first end to be seated around a head of a corresponding pedicle screw which is, in turn, coupled to a corresponding rod, whereby said means for securing said first end to said corresponding rod is a means by which the rod is secured to the pedicle screw.

4. The device as set forth in claim 1, wherein said hinge-post comprises a threading on an upper portion thereof.

5. The device as set forth in claim 4, wherein said at least one locking means comprises a nut which is mateable with said threading on said upper portion of said hinge-post, whereby the rotation advance of said nut on said threading provides the compression by which the at least two coupling elements are crush-locked together.

6. The device as set forth in claim 1 wherein said at least two coupling elements comprise two coupling elements, and wherein said at least one passageway mutually formed by the relative positioning of the elongate holes of said two coupling elements comprises a single passageway.

7. The device as set forth in claim 1 wherein said at least one hinge-post comprises one hinge-post, and wherein said at least one locking means comprises a single locking means.

8. A variable length cross-link device for use with orthopaedic rod apparatuses having a pair of rods, comprising:

at least two coupling elements each having first and second ends, said first ends of each having means for securing to alternative ones of said pair of rods, and said second ends having through holes;

a linkage member having a flat conformation and an elongate hole formed therein such that each of said at least two coupling elements is positionable relative to said linkage member such that said through hole in said second end thereof is disposed co-linearly with a portion of said elongate hole of said linkage member so as to form a passageway, and wherein said at least two of said at least two coupling elements form at least two spaced apart passageways with separate portions of said elongate hole of said linkage member;

at least two hinge-post members, each being positionable in a corresponding one of said at least two passageways, such that said at least two of said at least two coupling elements may translate relative to one another, and relative to the linkage member as said corresponding hinge-posts slide within said elongate hole, and such that said corresponding at least two coupling elements may angulate relative to one another and said linkage member via rotation around said corresponding hinge-posts; and at least two locking means, each being mateable with one of said at least two hinge-post such that when said locking means is engaged thereonto, each corresponding coupling element is compressed against said linkage member thereby being crush-locked together and prevented from further relative motion.

9. The device as set forth in claim 8, wherein said first ends of said at least two coupling elements comprises a hook-shaped conformation and wherein said means for securing same to alternate ones of said rods comprises a set screw.

10. The device as set forth in claim 8, wherein said first ends of said at least two coupling elements each comprises a circular hole which permits each of said first end to be seated around a head of a corresponding pedicle screw which is, in turn, coupled to a corresponding rod, whereby said means for securing said first end to said corresponding rod is a means by which the rod is secured to the pedicle screw.

11. The device as set forth in claim 8, wherein each of said at least two hinge-posts comprises a threading on an upper portion thereof.

12. The device as set forth in claim 11, wherein each of said at least two locking means comprises a nut which is mateable with said threading on said upper portion of the corresponding hinge-post, whereby the rotation advance of said nut on said threading provides the compression by which each of the coupling elements and the linkage member are crush-locked together.

13. The device as set forth in claim 8, wherein said at least two coupling elements comprise two coupling elements, and wherein said at least two passageways mutually formed by the relative positioning of the through holes of each coupling element with the elongate holes of said linkage member comprises two passageways.

14. The device as set forth in claim 8, wherein said at least two coupling elements comprise four coupling elements, and wherein said at least two passageways are formed by the mutual positioning of the through holes of pairs of said four coupling elements with the elongate holes of said linkage member comprises two passageways.

15. The device as set forth in claim 8, wherein said at least two hinge-posts comprises two hinge-posts, and wherein said at least two locking means comprises two locking means.

* * * * *